US005555305A

United States Patent [19]

Robinson et al.

[11] Patent Number: 5,555,305
[45] Date of Patent: Sep. 10, 1996

[54] METHOD AND APPARATUS FOR SECURE TRANSMISSION OF VIDEO SIGNALS

[75] Inventors: Adrian P. Robinson, London; Christopher K. P. Clarke, Crawley; Andrew J. Bower, Burgess Hill, all of United Kingdom

[73] Assignee: British Broadcasting Corporation, London, England

[21] Appl. No.: 211,279

[22] PCT Filed: Sep. 29, 1992

[86] PCT No.: PCT/GB92/01786

§ 371 Date: Jun. 13, 1994

§ 102(e) Date: Jun. 13, 1994

[87] PCT Pub. No.: WO93/07718

PCT Pub. Date: Apr. 15, 1993

[30] Foreign Application Priority Data

Sep. 30, 1991 [GB] United Kingdom .................... 9120696
May 20, 1992 [GB] United Kingdom .................... 9210750

[51] Int. Cl.⁶ .................................................. H04N 7/167
[52] U.S. Cl. .................................................. 380/14; 380/15
[58] Field of Search ........................... 380/15, 14, 17

[56] References Cited

U.S. PATENT DOCUMENTS

| | | |
|---|---|---|
| 4,081,832 | 3/1978 | Sherman . |
| 4,245,246 | 1/1981 | Cheung . |
| 4,405,942 | 9/1983 | Block et al. . |
| 4,410,911 | 10/1983 | Field et al. . |
| 4,528,589 | 7/1985 | Block et al. . |
| 4,563,702 | 1/1986 | Heller et al. . |
| 4,575,754 | 3/1986 | Bar-Zohar . |
| 4,608,456 | 8/1986 | Paik et al. . |
| 4,682,360 | 7/1987 | Frederiksen . |
| 4,694,489 | 9/1987 | Frederiksen . |
| 4,719,505 | 1/1988 | Katznelson . |
| 4,742,543 | 3/1988 | Frederiksen . |
| 5,144,663 | 9/1992 | Kudelski et al. . |
| 5,321,748 | 6/1994 | Zeidler et al. ............................ 380/14 |
| 5,335,275 | 8/1994 | Millar et al. ............................... 380/4 |

FOREIGN PATENT DOCUMENTS

| | | |
|---|---|---|
| 0046798 | 3/1982 | European Pat. Off. . |
| 0016125 | 2/1983 | European Pat. Off. . |
| 0116082 | 8/1984 | European Pat. Off. . |
| 0127383 | 12/1984 | European Pat. Off. . |
| 0127382 | 12/1984 | European Pat. Off. . |
| 0196724 | 10/1986 | European Pat. Off. . |
| 0243312 | 4/1987 | European Pat. Off. . |
| 0325509 | 7/1989 | European Pat. Off. . |
| 0345952 | 12/1989 | European Pat. Off. . |
| 0356200 | 2/1990 | European Pat. Off. . |
| 0443987 | 8/1991 | European Pat. Off. . |
| 2330236 | 5/1977 | France . |
| 2524242 | 9/1983 | France . |
| 2541841 | 8/1984 | France . |

(List continued on next page.)

OTHER PUBLICATIONS

Patent Abstracts of Japan, vol. 10, No. 125 (E–402) May 10, 1986 (JP A 60 256 286).
Patent Abstracts of Japan, vol. 13, No. 123 (E–733) Mar. 27, 1989 (JP A 63 292 788).
Patent Abstracts of Japan, vol. 15, No. 144 (P–1189) Apr. 11, 1991 (JP A 30 19176).

*Primary Examiner*—Stephen C. Buczinski
*Attorney, Agent, or Firm*—Kevin J. Fournier

[57] ABSTRACT

Video signals are sampled at 4Fsc locked onto sub-carrier phase and frequency. The active picture lines of each field are divided into 6 blocks of 47 lines and the active line periods of those lines scrambled on a block by block basis by line order shuffling. The shuffling algorithm is generated by a line shuffling permutator driven by a PRBS generator (controls 36, 38). Active line period samples for one block are written in unscrambled form into a first memory block (32) and samples from the previous block are read out in scrambled form from a second memory block (34) for transmission. The complementary process takes place in the decoder.

24 Claims, 12 Drawing Sheets

FOREIGN PATENT DOCUMENTS

| | | |
|---|---|---|
| 1503051 | 3/1978 | United Kingdom . |
| 2086181 | 5/1982 | United Kingdom . |
| WO81/02499 | 9/1981 | WIPO . |
| WO82/01109 | 4/1982 | WIPO . |
| WO83/04154 | 11/1983 | WIPO . |
| WO85/03401 | 8/1985 | WIPO . |
| WO90/10354 | 9/1990 | WIPO . |
| WO91/14341 | 9/1991 | WIPO . |

| INPUT SIGNAL | | TRANSMITTED SIGNAL | | OUTPUT SIGNAL |
|---|---|---|---|---|
| VBI 30 LINES | | | | |
| BLOCK 0 | 59L | | | |
| BLOCK 1 | 56L | BLOCK 0 | 59L | VBI |
| BLOCK 2 | 56L | VBI | 30L | BLOCK 0 |
| BLOCK 3 | 56L | BLOCK 1 | 56L | BLOCK 1 |
| BLOCK 4 | 56L | BLOCK 2 | 56L | BLOCK 2 |
| VBI | 29L | BLOCK 3 | 56L | BLOCK 3 |
| BLOCK 0 | 59L | BLOCK 4 | 56L | BLOCK 4 |
| BLOCK 1 | 56L | BLOCK 0 | 59L | VBI |
| BLOCK 2 | 56L | VBI | 30L | BLOCK 0 |
| BLOCK 3 | 56L | BLOCK 1 | 56L | BLOCK 1 |
| BLOCK 4 | 56L | BLOCK 2 | 56L | BLOCK 2 |
| VBI | 30L | BLOCK 3 | 56L | BLOCK 3 |
| | | BLOCK 4 | 56L | BLOCK 4 |
| | | BLOCK 0 | 59L | VBI |
| | | VBI | 30L | |

*Fig.1*

| INPUT SIGNAL | TRANSMITTED SIGNAL | OUTPUT SIGNAL |
|---|---|---|
| VBI (31 LINES) | BLOCK 0 (47 LINES) | VBI (31 LINES) |
| BLOCK 0 (47 LINES) | VBI (31 LINES) | BLOCK 0 (47 LINES) |
| BLOCK 1 (47 LINES) | BLOCK 1 (47 LINES) | BLOCK 1 (47 LINES) |
| BLOCK 2 (47 LINES) | BLOCK 2 (47 LINES) | BLOCK 2 (47 LINES) |
| BLOCK 3 (47 LINES) | BLOCK 3 (47 LINES) | BLOCK 3 (47 LINES) |
| BLOCK 4 (47 LINES) | BLOCK 4 (47 LINES) | BLOCK 4 (47 LINES) |
| BLOCK 5 (47 LINES) | BLOCK 5 (47 LINES) | BLOCK 5 (47 LINES) |
| VBI (30 LINES) | BLOCK 0 (47 LINES) | VBI (30 LINES) |
| BLOCK 0 (47 LINES) | VBI (30 LINES) | BLOCK 0 (47 LINES) |
| BLOCK 1 (47 LINES) | BLOCK 1 (47 LINES) | BLOCK 1 (47 LINES) |
| BLOCK 2 (47 LINES) | BLOCK 2 (47 LINES) | BLOCK 2 (47 LINES) |
| BLOCK 3 (47 LINES) | BLOCK 3 (47 LINES) | BLOCK 3 (47 LINES) |
| BLOCK 4 (47 LINES) | BLOCK 4 (47 LINES) | BLOCK 4 (47 LINES) |
| BLOCK 5 (47 LINES) | BLOCK 5 (47 LINES) | BLOCK 5 (47 LINES) |
| VBI (31 LINES) | BLOCK 0 (47 LINES) | VBI (31 LINES) |
| | VBI (31 LINES) | |

OVERALL DELAY = 47+47+31 = 125 LINES

Fig.2

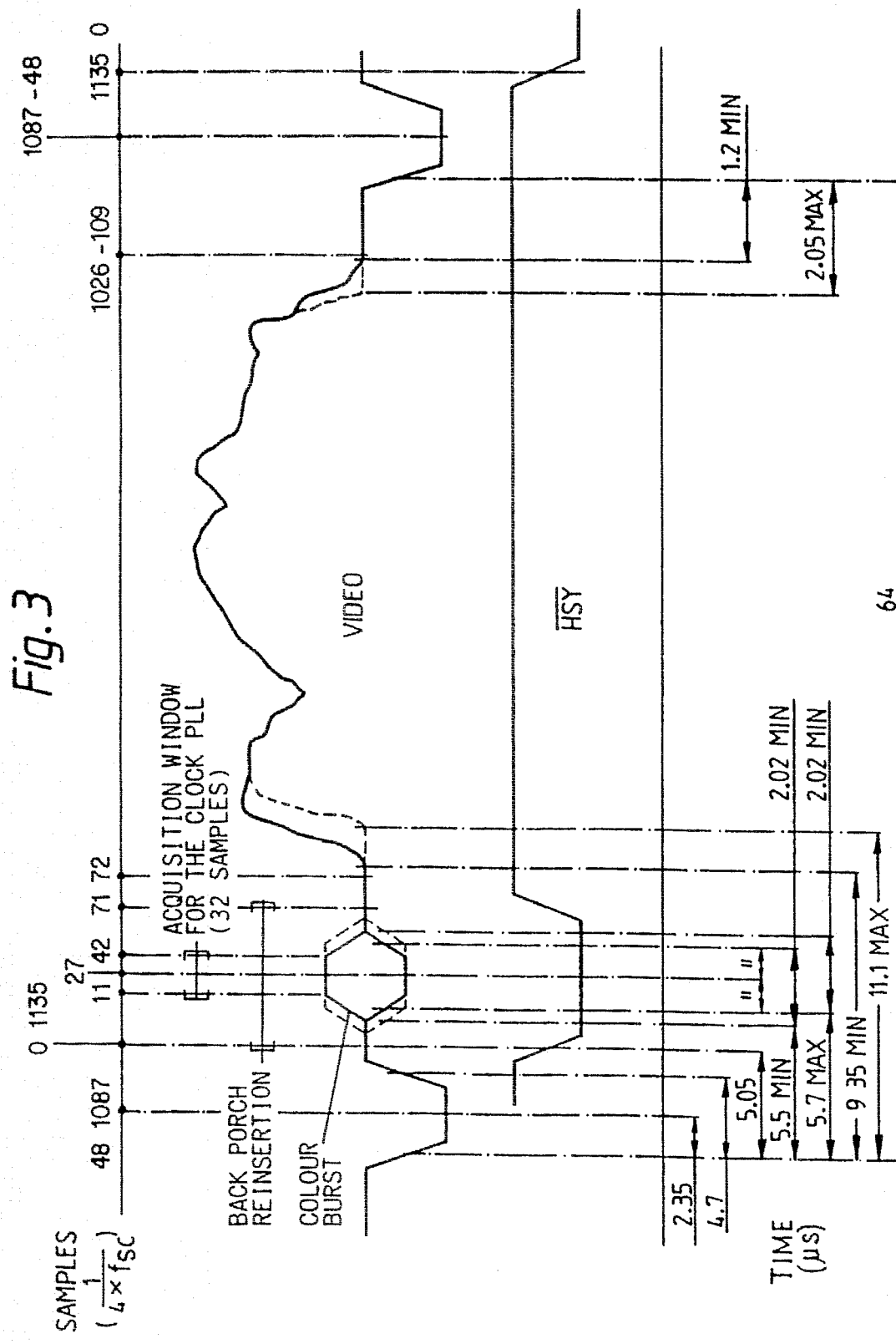

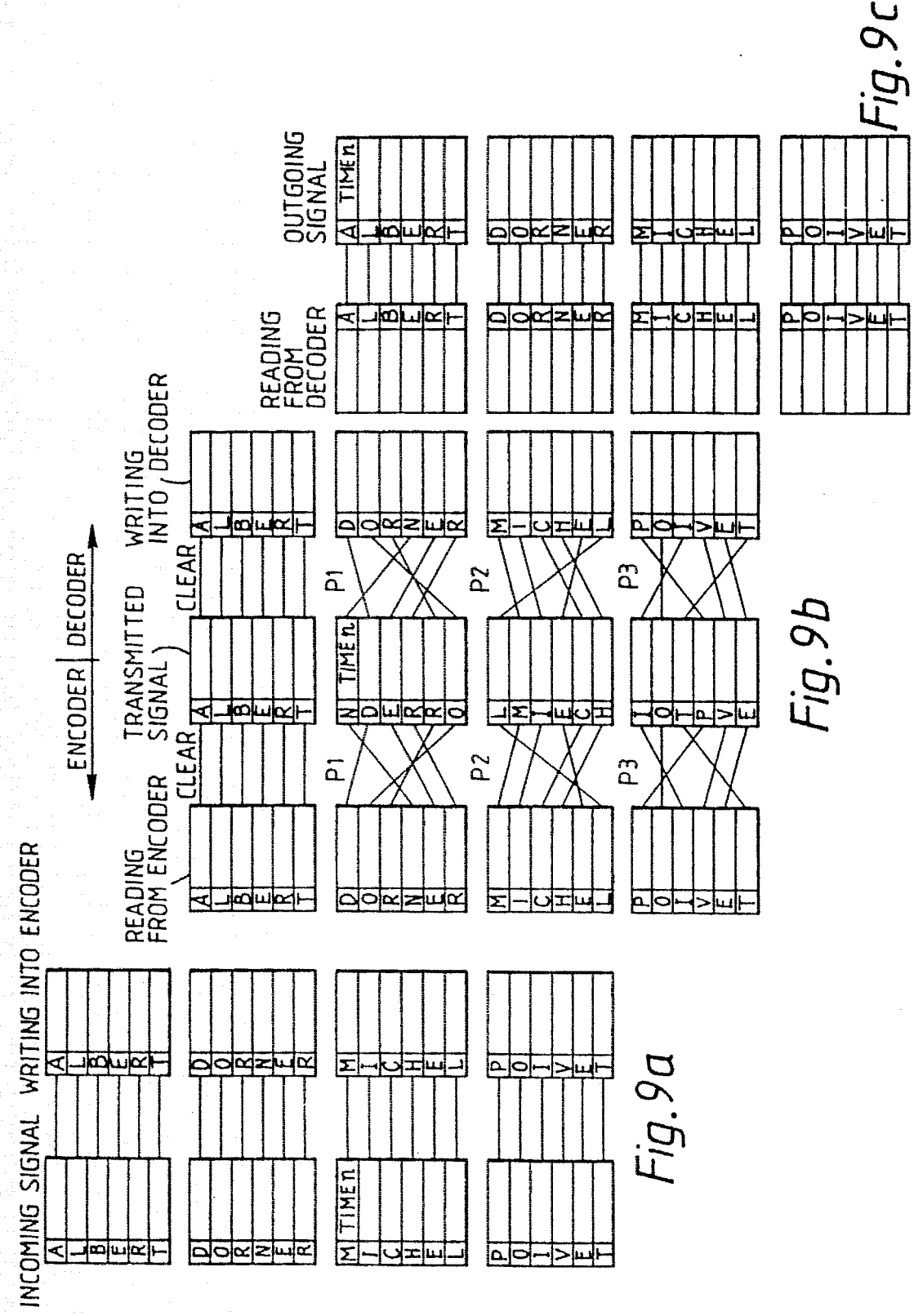

| DELAY TO OUTPUT | DELAY TO STORES' | STORE A | STORE B | CODER O/P | |
|---|---|---|---|---|---|
| 125 LINES | | | | 622 27 | VBI |
| | 31 LINES | WRITING BLOCK 2 | READING BLOCK 1 | 75 121 | BLOCK 1 |
| | 31L | READING BLOCK 2 | WRITING BLOCK 3 | 122 168 | BLOCK 2 |
| | 31L | WRITING BLOCK 4 | READING BLOCK 3 | 169 215 | BLOCK 3 |
| | 31L | READING BLOCK 4 | WRITING BLOCK 5 | 216 262 | BLOCK 4 |
| | 1L | WRITING BLOCK 6 | READING BLOCK 5 | 263 309 | BLOCK 5 |
| | 1L | READING BLOCK 6 | WRITING BLOCK 7 | 340 386 | BLOCK 6 |
| 125L | | | | 310 339 | VBI |
| | 31L | WRITING BLOCK 8 | READING BLOCK 7 | | BLOCK 7 |
| | 31L | READING BLOCK 8 | WRITING BLOCK 9 | | BLK 8 |
| | 31L | WRITING BLOCK 10 | READING BLOCK 9 | | BLK 9 |
| | 31L | READING BLOCK 10 | WRITING BLOCK 11 | | BLK 10 |
| | 0L | WRITING BLOCK 12 | READING BLOCK 11 | | BLK 11 |
| | 0L | READING BLOCK 12 | WRITING BLOCK 1 | | BLK 0 |
| 125L | | | | | VBI |

*Fig.11*

METHOD AND APPARATUS FOR SECURE TRANSMISSION OF VIDEO SIGNALS

FIELD OF THE INVENTION

This invention relates to the secure transmission of video signals. The invention is particularly concerned with the secure transmission of television signals from terrestrial transmitters.

BACKGROUND OF THE INVENTION

In recent years the advent of Pay-TV systems has generated a lot of interest in video scrambling. To operate a pay-TV system successfully, the video signal transmitted must be scrambled to a degree sufficient to render it unwatchable by a viewer not equipped with a suitable decoder.

There are a number of scrambled services in operation at present, for example that operated by B Sky B Limited which broadcasts from the Astra satellite.

The British Broadcasting Corporation has launched a subscription service to be broadcast at night time. The service uses existing terrestrial transmitters.

GB 1503051 describes the scrambling method used by the B Sky B service. The system, known as line-cut and rotate (LCR) scrambles individual video lines by cutting the line at a point determined by a pseudo-random binary sequence generator (PRBS) and rotating the two line halves so that the second half of the line is transmitted first. To decode the signal a subscriber must have a suitable decoder supplied with the cut point sequence. In practice the sequence is regenerated in the decoder using keys stored in a smart card which subscribers pay a fee to receive.

This scrambling system works well for satellite and cable services, and although used in terrestrial systems LCR may be found to be unsatisfactory under some conditions such as severe multipath propagation, line tilt etc.

An alternative to LCR is line shuffling (LS) in which the video signal is scrambled by shuffling the line order whilst maintaining the integrity of individual lines. Examples of line shuffling systems are disclosed in EP-A-356200 of Screen Electronics Limited and GB-A-2086181 of Telease Limited.

SUMMARY OF INVENTION

Although the applicants have appreciated that a system based on line shuffling is inherently more rugged than one based on line cut and rotate, neither of the LS systems referred to show how to provide a sufficient degree of ruggedness for use with terrestrial transmitters and receivers.

An aim of the present invention is to provide an encoding and decoding system based on a line shuffling system which is sufficiently secure and rugged for use with terrestrial broadcasts.

The invention in its various aspects is defined in the independent claims to which reference should be made.

In a system embodying the invention, the colour bursts of shuffled active video lines remain in position, unshuffled. This has a number of advantages. Firstly, the transmitted signal comprises a completely standard PAL signal as a result of which digital equipment in the transmission chain is not likely to be disturbed which might be the case if the bursts were scrambled. Secondly, security is improved as the line sequence cannot be deduced from measuring burst phase on successive lines.

Preferably analog video is sampled at four times the reference colour subcarrier frequency $F_{sc}$. Preferably the sampling is locked to the carrier phase and frequency. Prior art line shuffling systems adopt either 2 or 3 $F_{sc}$ sampling or line locked to ensure an integral number of samples per line. The use of $4F_{sc}$ in the PAL system produces 1135.0064 samples per line which can be compensated for by adding two extra samples on one line per field and has a disadvantage in that higher speed circuitry and greater memory storage is required.

However, with hardware costs falling neither disadvantage is of concern and $4F_{sc}$ subcarrier locked sampling has a number of advantages. In addition to the near integral number of samples per line, movement of lines within the sampling block leaves very few additional clues from the subcarrier phase as to how far a particular line has been moved; (It may allow lines to be divided into four groups according to whether displacement is 4n, 4n+1, 4n+2 or 4n+3 lines but no more).

Moreover, the use of $4F_{sc}$ sampling means that the sampling structure is picture locked and almost line locked. Anti-aliasing filters are less critical and there is less clock jitter than with line-locked sampling and therefore less chrominance jitter on the descrambled signal.

A further advantage of the invention is that it is possible to use a burst locked clock for sampling if the burst is unshuffled. Preferably, the active lines of each field are divided into an integral number of blocks and scrambles the signal by shuffling the line order within each block. Preferably, the number of lines in each block is the same. In one preferred embodiment six 47 line blocks scramble 282 lines of a 312½ line PAL field. A PAL field has 287½ active lines. Of the remaining 5½ lines, four carry data and the remaining 1½ are blanked.

The preferred scrambling structure has a number of advantages. As the blocks do not straddle the field interval the impact of field-interval distortion is minimised. Also, the block structure is locked onto the picture reducing flicker on the de-scrambled picture. This also means that the scrambled pictures have less flicker and so are less likely to precipitate a fit in individuals who suffer from photosensitive epilepsy.

As lines are scrambled within their blocks the range of displacement of any line is one block. This has the advantage of minimising the effects of transmission impairments on the descrambled signal.

Preferably, only the active line periods of active picture lines are shuffled.

The term active picture line used throughout the description and claims means lines which carry picture information as opposed to lines which comprise the vertical blanking interval. The term active line periods refers to those parts of active picture which carry picture information and excludes, for example, the line blanking interval.

Thus, in the preferred embodiment the line synchronising pulses as well as colour bursts are left unscrambled. In a preferred embodiment of the PAL signal example sampling at $4F_{sc}$ only 955 samples are shuffled. Preferably, these are samples 72 to 1026 inclusive but the cut points may vary in different embodiments between samples 61 and 75 and samples 1025 to 1039. The number of samples is not rigid but is preferably no more than 1024 to help memory management.

Embodiments of the invention in its various aspects will now be described, by way of example only, and with reference to the accompanying drawings, in which:

BRIEF DESCRIPTION OF DRAWINGS

FIG. 1 shows a first block structure for a line shuffling system;

FIG. 2 shows an alternative block structure of an input signal, transmitted signal and output signal;

FIG. 3 is a timing diagram for a signal scrambled according to a system embodying the invention;

FIG. 9 illustrates the permutation steps through the transmission channel;

FIG. 11 is a table showing how the delay of FIG. 10 operates on the coder;

DESCRIPTION OF BEST MODE

Figure 4:
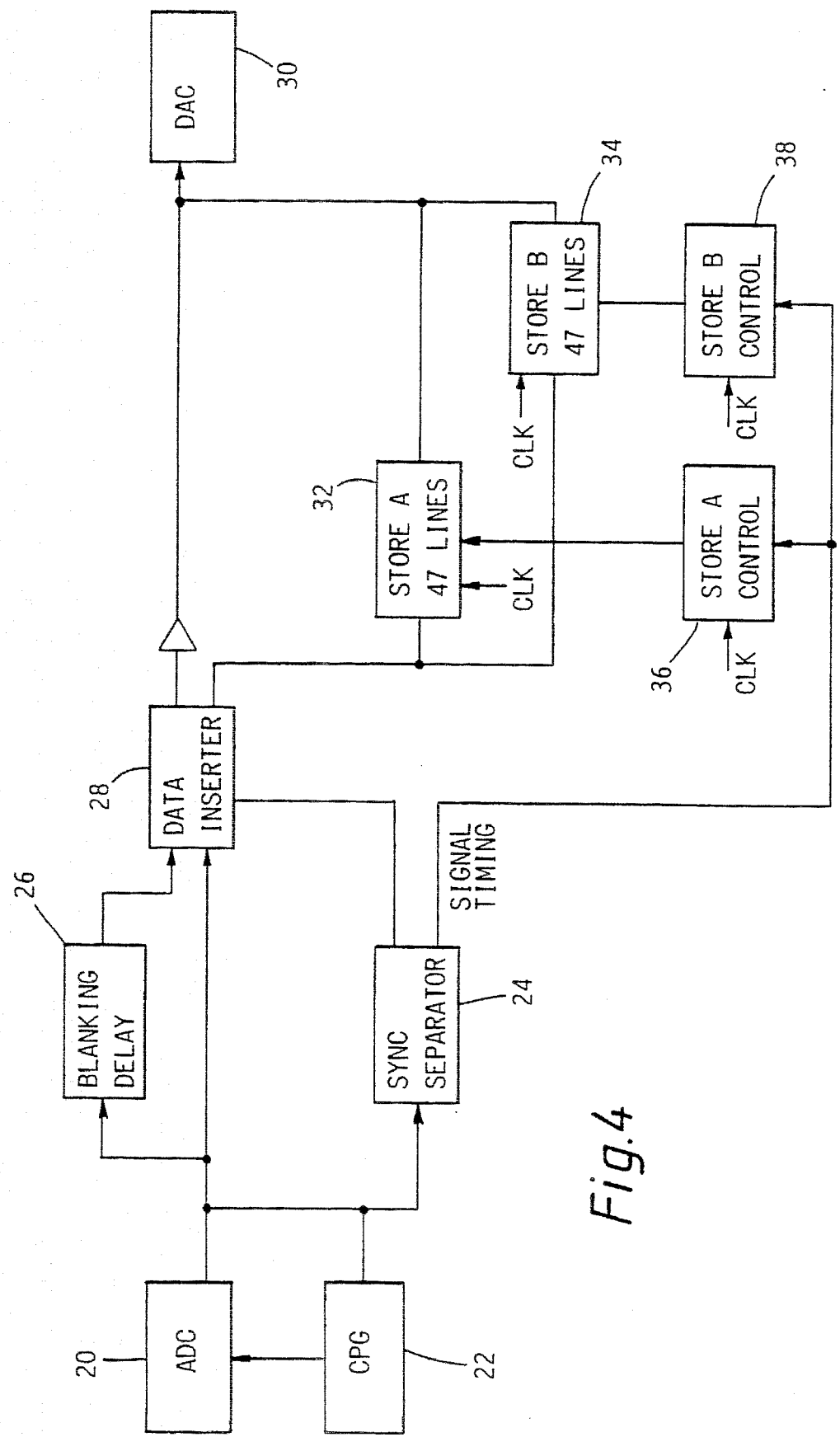
FIG. 4 illustrates an experimental coder embodying aspects of the invention.

The system to be described is suitable for scrambling PAL video signals. The principles are equally applicable to other systems such as NTSC, MAC and SECAM. The invention should not be construed as limited to any one video standard.

FIGS. 1 and 2 show two examples of line shuffling structures which embody one aspect of the invention. The prior art line shuffling systems either shuffle all the lines of a field in a single block or they divide the frames into a number of blocks of convenient size, for example, 32 lines. It has been found that neither approach is satisfactory and that the signal should be treated on a field by field basis such that each field comprises an integral number of blocks both in the clear and in the scrambled signal. A structure which involves blocks spanning or straddling the field blanking interval is more prone to field rate disturbances. Mixing lines from different fields in each block exaggerates any field interval distortion and can lead to differences between adjacent lines. The resulting line differences of the scrambled signal are too rapid to be corrected by receiver AGC. These line to line variations yield streaky noise on the descrambled picture.

Furthermore, as the block runs through the picture, distortion of the average picture level within a block, for example such as might arise through multipath propagation or transmitter impairments, can cause flicker on the descrambled picture.

The 625/50 PAL system is a 2:1 interlace signal in which each field comprises 312½ lines. Of these lines, 287½ are active picture lines and the remainder are the vertical blanking interval.

The line shuffling system proposed scrambles only the active picture lines. In FIG. 1 the active picture is broken down into 5 blocks, the first of which is 59 lines long and the remaining four 56 lines. Picture information from the remaining 4½ lines per field is discarded.

As it is more simple to process blocks which are all of equal size, the alternative shown in FIG. 2 comprises six blocks of 47 lines. As such a structure only contains 282 lines the 1½ remaining lines are discarded.

These structures also have the advantage that the active lines of the scrambled signal are advanced relative to the blanking intervals which avoids the need to store the field-blanking intervals in the decoder.

The structure adopted in FIG. 2 requires an overall delay of at least 125 lines between the input and output signals. The first field commences with an unscrambled blanking interval of 31 lines followed by six scrambled blocks of 47 lines. The transmitted signal comprises scrambled block 0 transmitted 78 lines after the beginning of the input signal (VBI=31 lines+Block 0=47 lines). This block is followed by the VBI and then scrambled blocks 1 to 5 and scrambled block 0 of the next field advanced with respect to the blanking interval. The output is again VBI followed by blocks 0–5 but delayed with respect to the input signal by two blocks and the VBI, a total of 125 lines. For the block structure of FIG. 1 the corresponding delay is 148 lines.

The block advance is not inherent in the block structures adopted, but it is desirable to avoid having to store the line blanking in the decoder. Where $4F_{sc}$ sampling is used this is especially important as it reduces the number of samples to be stored to less than 1024, so helping memory management and cost.

A further advantage of the block structure described is that the range of displacement of any line from its correct position is only one block. This mimimises the impact of transmission impairments on the descrambled picture as impairments tend to increase with the amount of displacement.

The PAL signal is supplied to the encoder in analog form and is digitised prior to scrambling. Prior line shuffling systems have used sampling rates of twice colour subcarrier frequency $2F_{sc}$ or $3F_{sc}$ or locked to the line.

The present system adopts a $4F_{sc}$ sampling structure, sampling at 17,734475 MHz and locked to both the frequency and phase of the PAL colour subcarrier. As an alternative, any integral multiple n.$4F_{sc}$ of $4F_{sc}$ could be used, for example $8F_{sc}$. However, processing speeds and memory costs may prohibit $8F_{sc}$ and greater values of n at present.

The use of $4F_{sc}$ sampling provides a number of advantages which make its adoption attractive. It results in a convenient sampling structure, which gives an almost whole number (1135) of samples per picture line, which can be locked to a particular phase of the colour sub-carrier. The use of a higher sampling frequency at $4F_{sc}$, as opposed to $2F_{sc}$ or $3F_{sc}$, means that anti-aliasing filters for the analogue-to-digital converters (ADCs) and the digital-to-analogue converters (DACs) will be less critical, than would be the case for a lower sampling frequency.

From the point of view of security, the use of $4F_{sc}$ sampling has the advantage that movement of lines within the scrambling block leaves no additional clues from the sub-carrier phase as to how far a particular line has been moved. There are, of course, some disadvantages to using $4F_{sc}$ sampling as opposed to a lower multiple of $F_{sc}$, namely that digital circuitry must be capable of operating at a higher speed, and that more video memory capacity is required. However, the convenience of using $4F_{sc}$ sampling is such that the advantages out-weigh any disadvantages.

The use of chrominance sub-carrier phase and frequency locked sampling has the advantage that there is less clock jitter than line-locked sampling and hence less chrominance jitter on the descrambled signal.

In fact, at $4F_{sc}$ the number of samples per line is 1135.0064. If all lines were regarded as containing 1135 samples there would be 0.0064×625=4 samples per frame which did not belong to any line. This can be avoided by including two extra samples on one line per field, that line having 1137 samples.

There will necessarily be a line by line shift between the real video timing, as expressed by the signal pulse and the pixel counter in view of the 0.0064 pixel remainder. At $F_{sc}$=4.43361875 MHz this shift is $$0.0064 \times \frac{1}{4F_{sc}} = 0.36 \, nS$$

per line.

For a block of 47 lines this delay is 17 nS and for a block of 59 lines 21.nS. In the 59/56 block example the blocks are advanced by this amount relative to the blanking intervals. This shift can be automatically compensated for by the descrambling process.

As mentioned previously, only the active picture lines are scrambled. However, of these lines, only the samples which comprise the active line period are scrambled. These are shown in FIG. 3. Thus samples 1 to 71 are unscrambled, samples 72 to 1026 are scrambled (955 samples) and samples 1027 to 1135 are unscrambled. Prior to scrambling, the samples are digitised. The advantage of this structure is that the colour burst of each line is not scrambled so that the transmitted signal is a completely standard mathematical PAL signal. There is no danger of the digital equipment in the transmission chain being disturbed as it might be if presented with a scrambled sequence of colour bursts. Moreover, the security of the system is increased because the phase of the colour bursts on successive lines will give no clues to line re-ordering. The use of unscrambled colour bursts makes the use of phase locked sampling more easy to implement as the clock can be locked to the colour burst.

The cut points can vary with different embodiments. The points may be chosen to be between samples 61 to 75 and samples 1025 to 1039.

Sampling points are at 45° points of the reference sub-carrier. That is, at the peaks and zero crossings of an ideal colour burst. This minimises the coding range required for each sample.

In order that the decoder can descramble the signal Videocrypt data, which carries signal information and decoding instructions must be transmitted with the signal. This may be done by assigning 4 lines of each field as data carriers. The data can be carried in the active picture which increases compatibility with existing transmission standards and equipment. The decoder will blank the data lines prior to display.

Thus, for the 47 line block, the video signal structure is as follows:

| line no | function |
| --- | --- |
| 623 2nd half- 23 2nd half | vertical blanking interval |
| 311–335 | |
| 23 2nd half, 310, 622, | blanked by encoder |
| 623 1st half | |
| 24–27, 336–339 | Videocrypt data |
| 28–209, 340–621 | carries active line parts scrambled in 47 line blocks. |

Scrambling of lines within a block is effected by permuting the order of transmission of the lines within each block. The control word for the permutation generator changes from block to block according to the output of a pseudo-random binary sequence generator PRBS. The PRBS is preferably initialised once every TV picture according to a 20 bit seed value. Thus 12 values are generated by the PRBS each picture, one for each block.

Because in the PAL system colour information is transmitted in phase relation between the burst and the active video subcarrier a very stable phase locked loop PLL is required. Active line periods are replaced by shuffled lines and chrominance noise will be present if there is any significant error. Permissible errors in timing are less than 1.5 nS which corresponds to a error of about 2°. The required accuracy is helped by measuring phase error only during those lines with a colour burst (lines 7 to 309 and 320 to 621).

The phase lock loop will be described in detail later in the description.

Referring now to FIG. 4, the operation of the codec may be best understood by consideration of an experimental coder which does use a PRBS and permutation generator as store controller, producing direct and permutated address sequences as required.

The architecture of the coder and decoder is necessarily almost identical, the major difference being that the line and field blanking intervals are delayed in the coder but not in the decoder and although the following description is directed to the coder the decoder operates in the same manner.

To be compatible with conventional terrestrial transmitting standards the scrambled picture is transmitted as an analog signal. The received scrambled signal is first converted into digital format by analog-to-digital convertor 20. The ADC is regulated by a clock pulse generator CPG 22 to sample the received signal at $4F_{sc}$. The ADC and DAC in the decoder uses 8 bit video samples. The clock pulse generator is frequency and phase locked to the colour burst signal sampling at 45° points as described previously. A suitable clock pulse generator is a voltage controlled crystal oscillator VCXO producing on $8F_{sc}$ signal together with a divide-by-two circuit to produce an output signal at $4F_{sc}$ with a 1:1 mark-space ratio.

The ADC may be based on a TRW TDC 1007 ADC which can operate at frequencies up to 25 MHz. The coder ADC is a 10 bit ADC which is the standard for professional equipment.

Stabilisation of the frequency and phase of the master clock signal relative to the colour burst of the sub-carrier is performed internally in the c.p.g. 22. A sync. separator 24 produces the necessary timing signals associated with the video wave form such as mixed sync. line pulses and identifies odd and even blocks.

The output of the ADC is input in parallel to a blanking delay unit 26 which delays the blanking interval and to data inserter 28 which also receives the delayed output from the blanking delay 26. The data inserter 28 has an output directly to output Digital to Analog Convertor DAC 30 and also to 47 line stores A and B 32, 34. The stores are controlled by respective store controls 36, 38 which are controlled by clock and sync. signals provided by the sync. generator. The store controls control the reading and writing of data from and to the respective memory store and are provided with the scrambling sequence. The store controls comprise a PRBS generator and a permutation generator.

Figure 10:
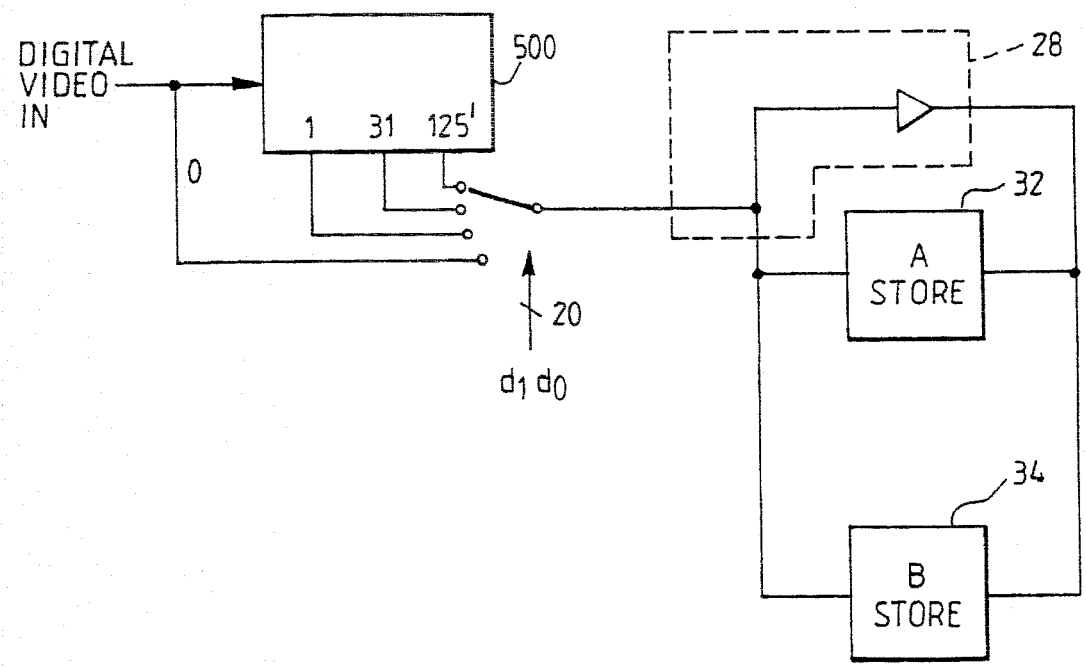
FIG. 10 shows the coder blanking delay in more detail.

The blanking delay element 26 of the coder is illustrated in greater detail in FIG. 10. The delay performs two functions: firstly, it provides a 125 line delay for the samples corresponding to the vertical and horizontal blanking; secondly it provides a variable delay for the samples comprising the active line periods of the active picture lines. This latter feature enables the shuffling to be performed with only two blocks of memory. FIG. 10 shows how a switchable delay 500 of 0, 1, 31 and 125 lines delay time is used for the 47 line block structure.

The blanking delay 500 takes in the video from the ADC and passes it on directly or delays it by approximately 1, 31 or 125 lines; the exact delays required are 1135, 35187 or 141,877 samples.

The delay is selected by two control lines d1 and d0 according to the following:

| d1 | d0 | delay |
|----|----|-------|
| 0  | 0  | 0     |
| 0  | 1  | 1135  |
| 1  | 0  | 35187 |
| 1  | 1  | 141877|

An additional fixed delay for pipelining can be added to all the outputs without problem. The delay has to change on a sample by sample basis. Since all the delay values are odd, the delay could be achieved by demultiplexing by two into two 128k×8 static RAM devices. Thus each device would only be required to read or write in a clock period, with a corresponding relaxation of timing.

If the samples are numbered 0 to 1134 on each line (except lines 312 and 624, which are numbered 0 to 1136), then samples containing the sync and burst waveforms, 1117 to 171, are always taken from the 125 line delay address. This delay is also used during the VBIs (lines 622 to 27 and lines 310 to 339) for samples 172 to 1116. The active samples 172 to 1116 of the lines from delay, those of Blocks 6 and 7 (lines 340 to 386 and 387 to 433) are taken with a 1 line delay, whilst all the other blocks are taken with a 31 line delay.

FIG. 11 shows how the blanking delay operates in the coder to ensure that the VBI period is the correct number of lines, 30 or 31.

Figure 12:
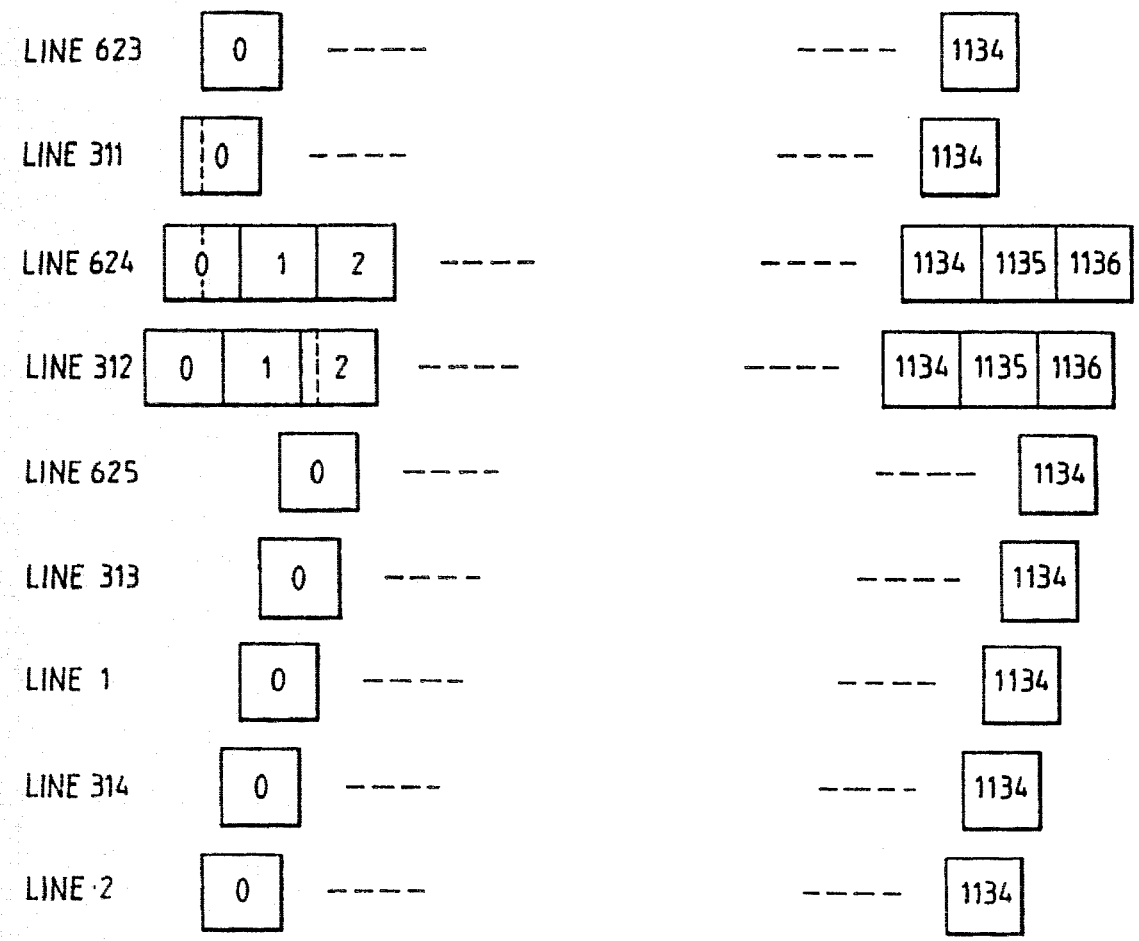
FIG. 12 shows how extra samples are inserted into two lines per picture.

FIG. 12 shows how the $4F_{sc}$ samples are arranged with respect to each other around lines 624 and 312 which are the long 1137 sample lines.

The scrambler coder operates by allowing incoming line and field blanking signals to pass straight through to the DAC to the output. The remaining active portions of the active lines (955 samples) are stored in the stores 32, 34. The first block, block 0 of FIG. 1(*b*) is stored in store 32 and the next block, block 1 is stored in block 34. It is important to note that the samples are stored in the stores in clear; that is in unscrambled form. As the lines of block 1 are being stored in store 34, the lines of block 0 are read out from store 32 under the control of control 36 in scrambled form. Thus, the read addressing is scrambled but the write addressing is in clear. When block 1 has been written into store 34 block 0 will have been read from store 32 and block 2 can be written, again in clear, to store 32 while block 1 is read from store 34. The output of the two stores is fed into DAC 30. The critical timing described previously is such that the scrambled active line portions are re-inserted into the unscrambled blanking intervals with a minimum degree of error.

The descrambler operates in a complementary fashion. During each picture, the active picture lines of incoming scrambled video are written to either the "A" or "B" store in descrambled order using the same sequence of addresses as in the scrambler. As in the coder, the line order is provided by a PRBS and permutation generator which comprise Store Controls 36, 38 to produce the memory addressing and control signals. This effectively descrambles the incoming video signal. At the same time, samples written to the other store during the previous block are read out to the DAC to produce a descrambled output signal. Once again the two RAM stores swap between the writing and reading functions on alternate blocks.

It is important to note that at the coder the scrambled active picture line output signals are delayed at the stores relative to their own line syncs and colour bursts. Similarly, in the decoder the output descrambled signal is delayed relative to the syncs and burst of the received scrambled signal in the stores. Synchronisation is achieved by delaying the blanking intervals appropriately in the coder.

The stores used in the encoder and decoder may conveniently be 10 and 8 bit dynamic RAMs respectively. SRAMs or VRAMs may also be used. The DAC may be a 10 bit (encoder) or 8 bit (decoder) device for example a TRW TDC 1016 J which can operate at speeds of up to 20 MHz.

Figure 5:
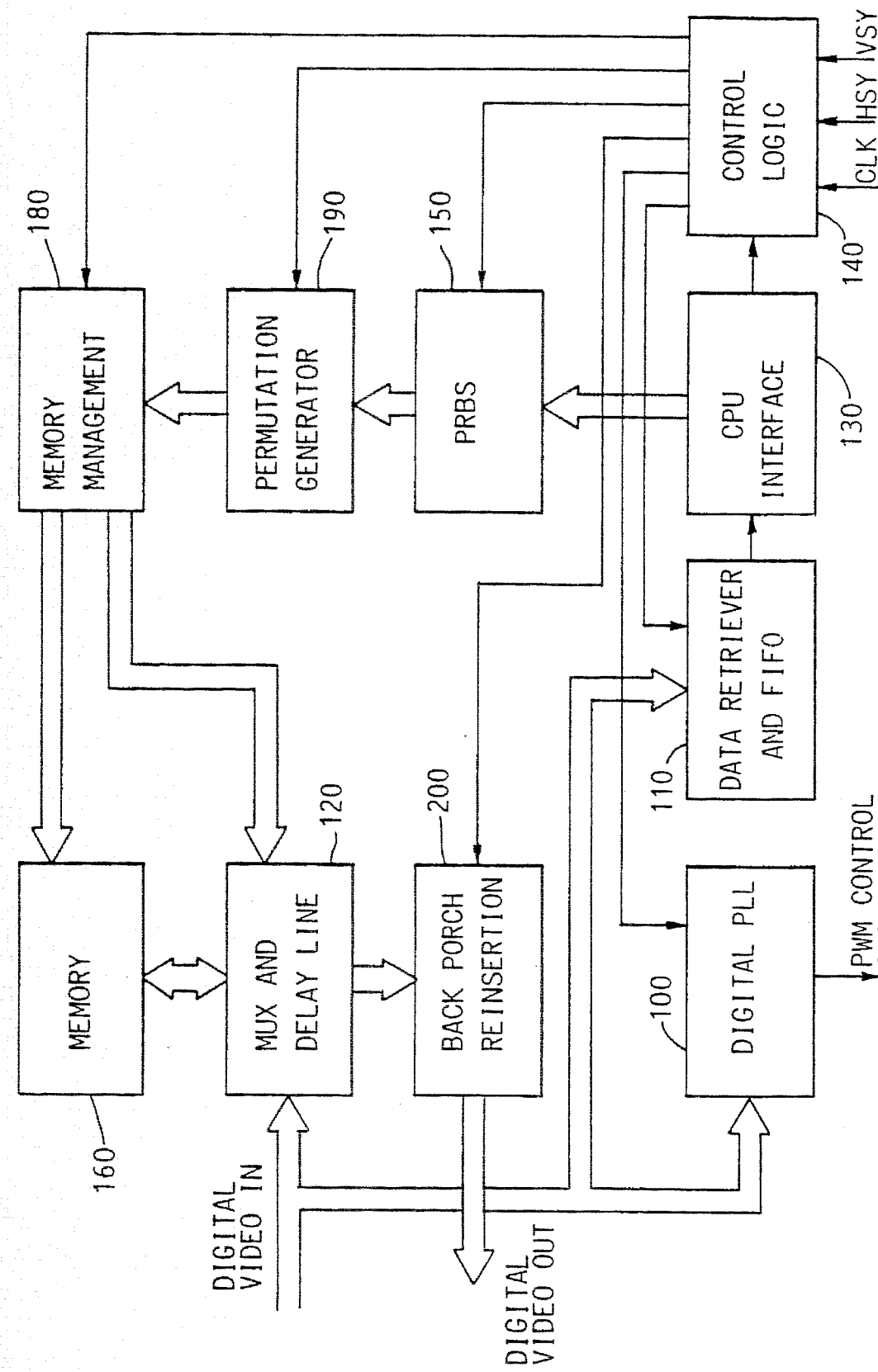
FIG. 5 illustrates, in block form, the digital portion of a production decoder.

Referring now to FIG. 5, the digital portion of a production decoder is illustrated. The corresponding encoder is substantially identical.

An incoming scrambled video signal is first digitised in an ADC (not shown) and then fed to the phase lock loop 100, the Data retriever 110 and a multiplex and delay line 120. The data retriever 110 retrieves the Videocrypt data transmitted on lines 24–27 and 336–339. The mux and delay line is required to support the memory 160 which is a VRAM. The retrieved data is fed to the system CPU 130 which also interfaces with control logic 140 and PRBS 150. The control logic manages the timing of all elements of the system, with the exception of the memory 160 and delay line 120. The control logic is supplied with the system clock at $4F_{sc}$ and horizontal and vertical sync. signals HSY and VSY. The memory 160 comprises two 47 line blocks which operate in the manner described in the previous example. Memory management 180 controls the read and write addressing and is described in greater detail with reference to FIGS. 7 and 8. The memory management is controlled by the permutation generator 190, itself under the control of PRBS 150 the PRBS and permutation generator are shown in greater detail in FIGS. 14a)–c) and 15. The construction of the permutation generator and the PRBS may be of any desired form and is well documented in the art. The memory again stores the active line period data in clear and the output is multiplexed back onto the unscrambled portions of the signal. Prior to D-to-A conversion and output the back porch of the signal is re-inserted at 200. The black level reinsertion circuit is shown in more detail in FIG. 6.

The back porch reinsertion is necessary in the decoder to ensure that clamps in circuitry downstream have a clean backporch for clamping. If this is not done in a line shuffling system, transmission impairments such as multipath can cause the clamping process to introduce streaky noise. The colour burst is passed on to the PAL decoder in the receiver without modification so that automatic colour correction circuits, which measure the amplitude of the burst, operate correctly and is easier than generating a new burst.

Figure 6:
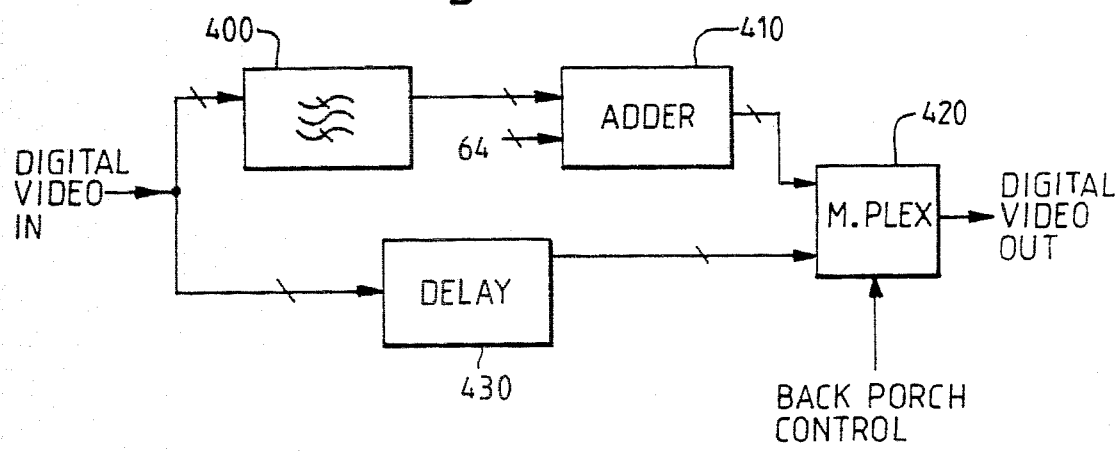
FIG. 6 shows in block form, the back porch reinsertion circuit of the decoder of FIG. 5.

In FIG. 6 back porch reinsertion is performed using digital filtering techniques. The input video signal is fed through a chrominance band pass filter 400, to the output of which is added the prescribed black level value of 64 in adder 410. This signal is selected during the back porch by a control signal from the sync. separator which operates on multiplexer 420. The multiplexer has as its other input the digital video input delayed by compensating delay line 430 by the signal path delay through the filter 400 and adder 410. The delayed video is selected in the multiplexer at all times except the back-porch interval.

FIGS. 4 and 5 have been described with reference to a 47 line block size. Suitable modification would be neccessary for the 56/59 line example referred to previously or any other block size and will be clear to one skilled in the art.

Figure 7:
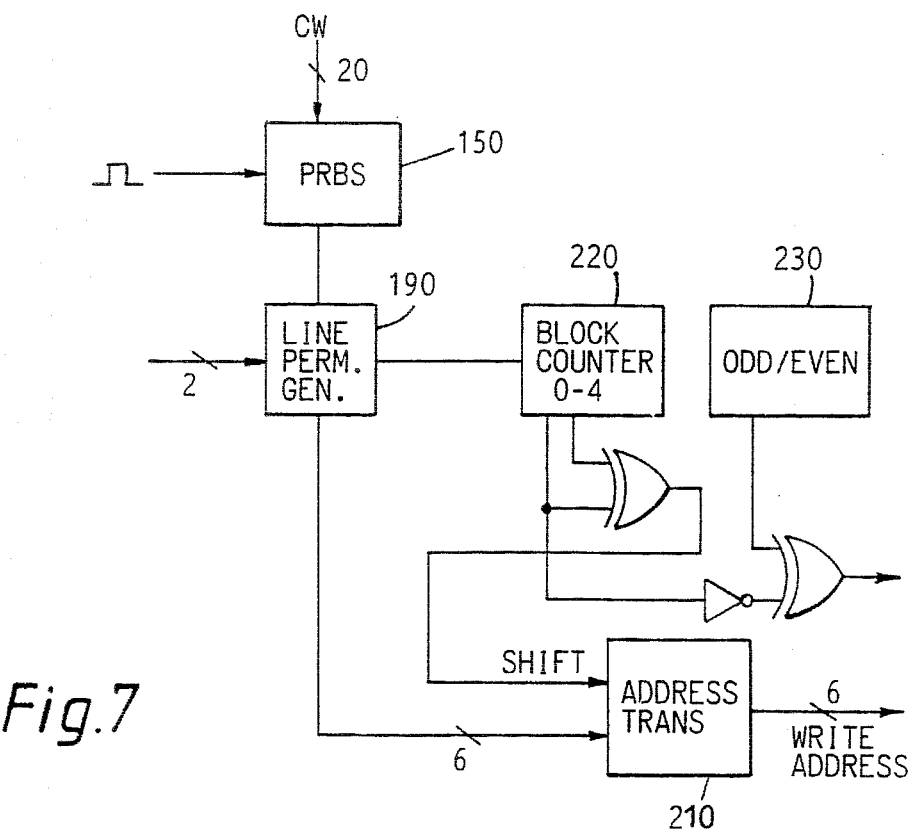
FIG. 7 shows the write address circuitry for the memory of a 56/59 line block decoder.

FIG. 7 shows the write address circuitry for the decoder required to write a scrambled signal in clear in the memory. The circuit shown is suitable for a 56/59 line block size.

Figure 8:
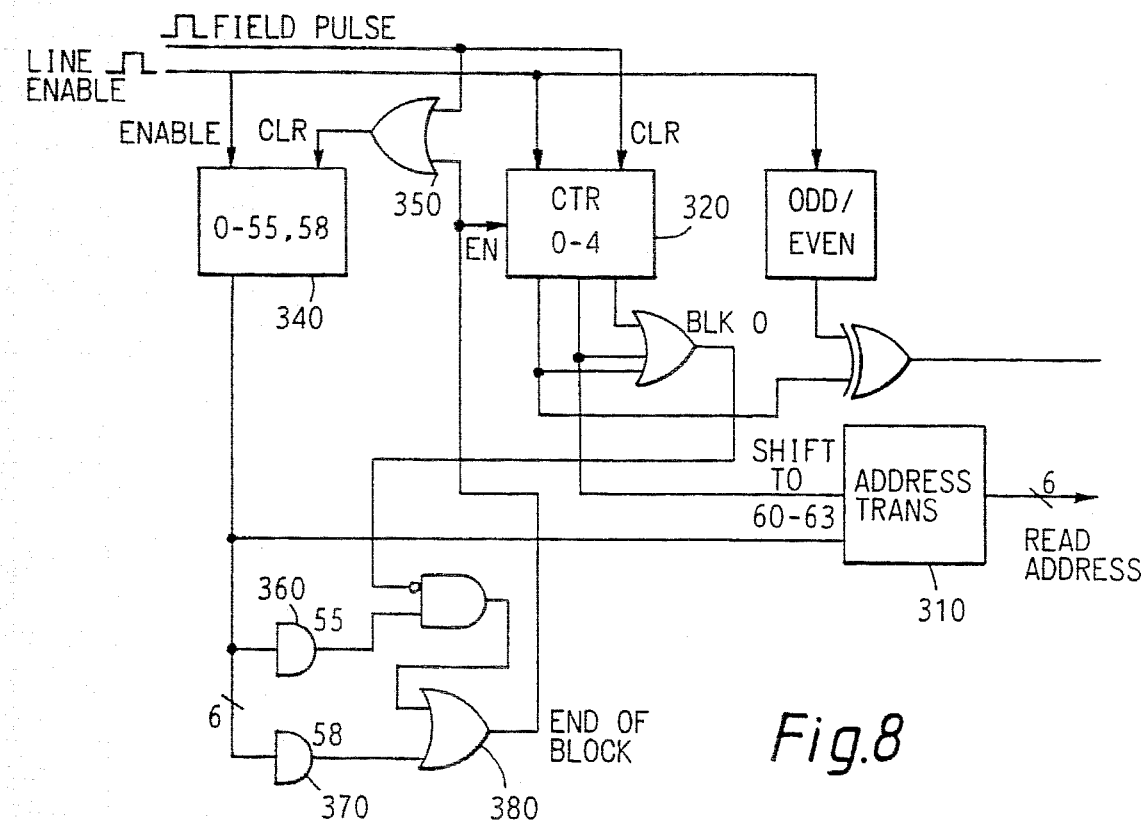
FIG. 8 shows the read address circuitry for the memory of system using a 56/59 block structure.

FIG. 8 shows the read address circuitry for the decoder which reads from the memory to provide the output to a MUX 120 in FIG. 5. In this example the circuitry is suitable for a 56/59 line block structure to illustrate the additional circuitry required to cope with blocks of different sizes.

Referring to FIG. 7 the 20 bit control word CW vis fed from the CPU to the PRBS 150 which controls the output of the line permutation generator 190. The generator 190 provides a six bit output to the address translator 210. As unequal block sizes are used 3 blocks overlap in the decoder as well as the encoder. The address translator moves the overlapping parts to an otherwise unused area of RAM. A block counter 220 steps from 0 to 4 and produces a shift input to the address translator to ensure that address are provided for the alternate block after each block of 47 lines. An odd/even counter 230 having an input from the block counter provides a 1 bit output to switch between memory blocks 32, 34 (FIG. 4) which is necessary as there is an uneven number of blocks per field.

The 56/59 block example may operate with the two blocks of memory being field stores, in which case the odd/even counter can be clocked from the field pulse. As block size changes counter 220, which steps from 0 to 4 must provide a signal to the generator 190 that the block size increases to 59 lines for the 4th block.

FIG. 8 shows how the odd/even counter 230 may be clocked in the 56/59 line example. A counter 340 steps between 0–55 and 0–58 depending on block size and provides an output to the address unit 310. The counter is cleared by a high output from OR gate 350 which has field pulse and end of block inputs. The end of block pulse is provided when the six inputs to either AND gate 360 or AND gate 370 go high, indicating that the count has reached 55 or 58 respectively.

These outputs provide the input to OR gate 380 whose output is the 'end of block' pulse. The output of gate 380 is also used to clock the block counter 320, which, in this instance, steps between 0–4. The remainder of the circuitry operates as described with reference to FIG. 7.

Figure 13:
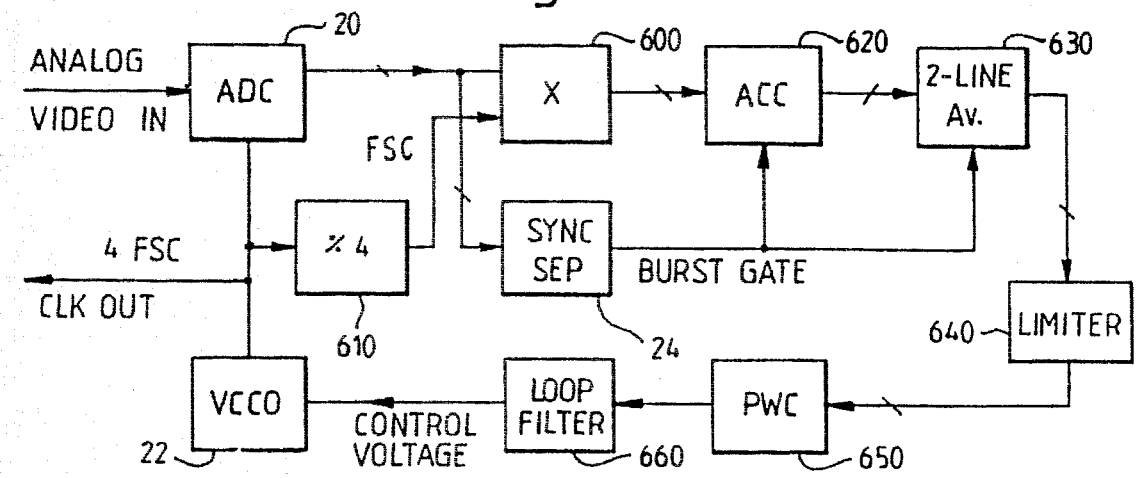
FIG. 13 is a block diagram of the phase lock loop of FIG. 5.

The digital phase lock loop is shown in FIG. 13. The ADC, clock generator and sync. separator are referred to by the same references as FIG. 4.

The digital output of ADC 20 is fed to a multiplier (controller generator) 600 which receives as its other input a pulse train at $F_{sc}$ derived from the $4F_{sc}$ clock and a divide by four logic unit 610. The output from the multiplier is passed to a 32 byte accumulator 620, a two line averager 630 a limiter 640, pulse width modulator 650 and loop filter 660 which supplies a control voltage to the voltage controlled crystal oscillator of the clock pulse generator 22. The accumulator 620 and 2 line averager 630 are controlled by burst gate signals from the sync. separator 24.

The accumulator 620 both adds and subtracts two successive bytes, calculating 32 samples for each burst, corresponding to samples 11 to 42 in FIG. 3. The samples are taken from the middle of the burst.

The averager determines the phase error of the PLL summing the accumulator output over the previous 2 lines and retaining the information for one line. The accumulator 640 reduces the dynamic range of the signal so that quantisation to eight bits is sufficient. The pulse width modulator 650 produces a binary sequence whose average corresponds to the measured error. The PWM 650 may alternatively be a pulse density modulator, a rate multiplier or a DAC.

The digital burst phase detector may be implemented in a number of different ways and the embodiment illustrated is just one example. The sync. separator may be analogue or digital or a combination of the two.

The control logic 140 in FIG. 5 and the sync separator 24 in FIG. 4 may be based on sync signals generated by analog sync separation. It has to be ensured that resynchronisation of the control logic occurs only when the system is out of tolerance with the incoming line pulses by more than a specified range of timing, as frequent resynchronising would disturb the decoded picture unnecessarily.

The time difference between a respective line in two adjacent fields is monitored. If the pulse from the sync separator arrives one field later within duration of the synchronisation window the system is working satisfactorily and does not need to be re-synchronized. The time difference between two adjacent lines is not evaluated because of the non-integral number of samples per line. The size of the window can be reduced where Videocrypt data rate is high. A similar reduction of the time for which the window is open is also required, if two or more integrated circuits are used for scrambling in the encoder, to achieve a high time precision. In the decoder the window size is advantageously chosen according to the reception quality to have a minimum degree of interference caused by data reception quality (time precision requires a short window) and re-synchronization, i.e. image quality (requires long window).

The synchronization window described can be switched off so that synchronization occurs every line. This can be used in an encoder where two Videocrypt chips with 8 bit video resolution are working in parallel to achieve a broader data bus, e.g. 10 bits for studio quality. In this case the horizontal reference for the second chip is generated by the master chip, whereby both chips work completely synchronously.

FIGS. 9a) to 9c) to shows how the different permutation steps work. FIG. 9a) shows how blocks are written into the encoder memory in clear. The first block is transmitted in clear but the second block undergoes a first permutation under control of the PRBS and permutation generator and is transmitted in scrambled form. However, due to the write address circuitry described with reference to FIG. 7, the block is written in clear in the decoder memory. Similarly subsequent blocks undergo different permutations P2, P3 etc. but are written in clear into the decoder. FIG. 9b shows that the reading from the decoder and the outgoing signal are identical but that block 0 (ALBERT) is output at time n, the time of input block 2 (MICHEL) illustrating the two block delay in the 47 line examples.

The embodiment as described transmits pictures fully scrambled on every field. In some instances it is desirable to use partial scrambling only. For example the program provider may wish to interest non-subscribers by showing them sufficient low quality pictures for them to subscribe. The embodiment may be operated in one of two further modes to achieve this aim without disrupting the regular decoded picture when changing the scrambling mode.

The first option is a 'clear delayed' mode in which the lines of each block are not scrambled but the picture is transmitted one block in advance. This has the effect that the bottom 47 lines of the picture appear at the top of the screen and the colour of the picture is false. Although very annoying to a regular subscriber, the viewer can discern sufficient detail to generate an interest in the programme being transmitted.

The second mode is 'flash mode' in which alternate fields are scrambled and the intervening fields transmitted in clear delayed mode. The effect on the transmitted signal is to have the clear delayed picture with a superimposed scrambled picture.

In view of the nature of scrambling process, it is not possible to change between fully clear and fully scrambled modes without losing one block of information. Transmitting in one of these two semi-scrambled modes enables the pictures to be shown in part to non-subscribers without disturbing the decoded picture.

Figure 14A:
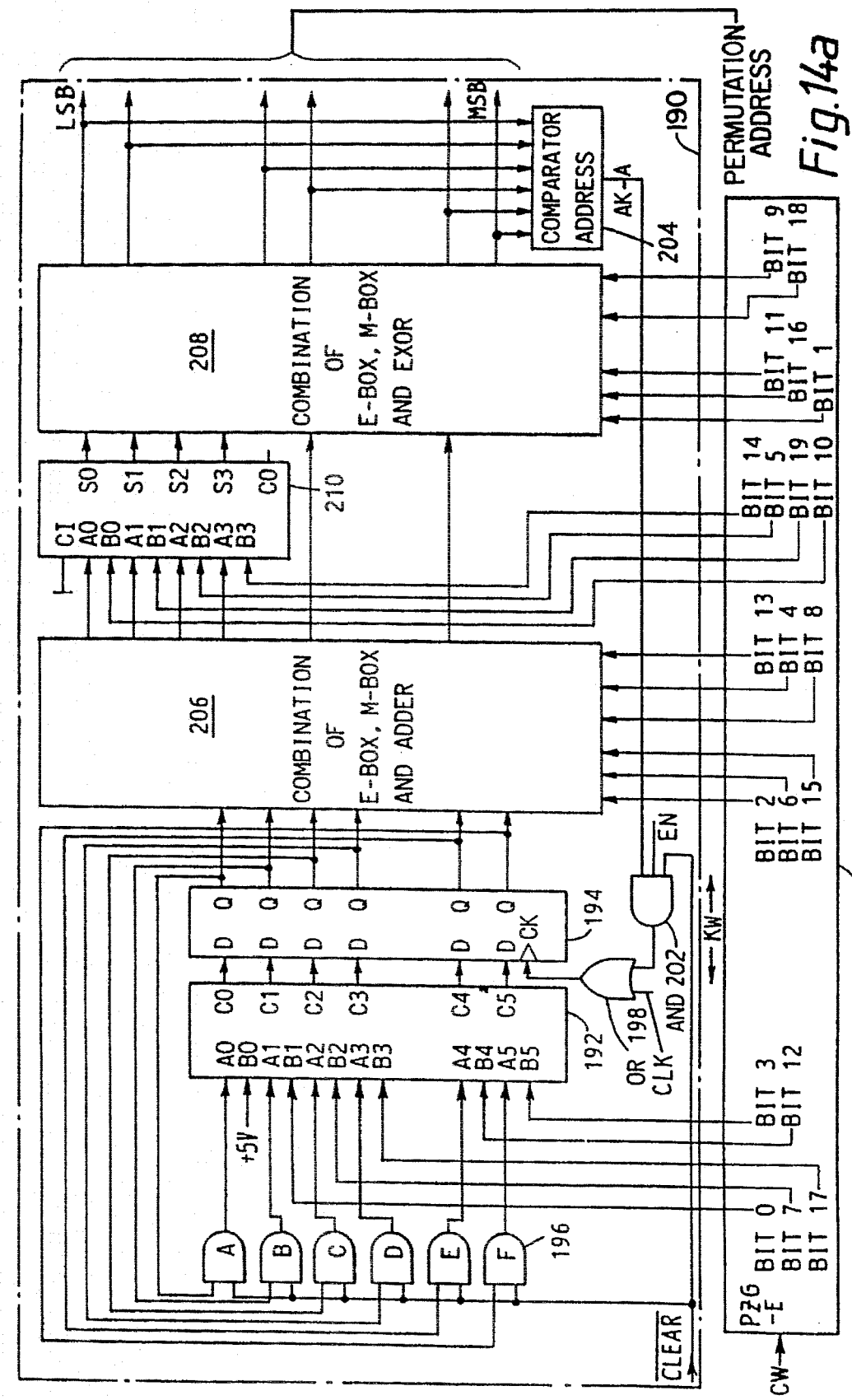
FIG. 14a) shows a circuit diagram of a permutation generator and pseudo random binary sequence generator embodying one aspect of the invention.

Referring now to FIGS. 14a)–c) and 15 the permutation generator 190 and pseudo-random binary sequence generator PRBS 150 are shown in more detail.

The pseudo-random generator PRBS 150 has e.g. n=20 binary outputs BIT0 . . . BIT19. The number of possible states of the pseudo-random generator PRBS is thus $2^{20}$= 1048576. A control word CW from the CPU interface 130 is applied to the pseudo-random generator PRBS via an input PZG-E, and a predetermined state is assumed on each occasion. This state which defines each output of the PRBS is referred to as a keyword KW. Every 40 ms a new control word different from the preceding and following control words is transmitted with the television signals and every 40 ms a part of this control word is applied to the pseudo-random generator.

The permutation generator 190 of FIG. 14a) has a clear input, which is set to zero in an initialisation phase of the permutation generator and serves to define the circuit state of the circuit arrangement.

The circuit arrangement 190 comprises a six-bit adder 192 with inputs A0 . . . A5, whose values are added to the values on the inputs B0 . . . B5 five of which, B1–B5 are provided by the five output bits 0, 7, 17, 12, 3 of the pseudo-random generator 150. The sixth input, B0, of the adder 5 is permanently at 5 volts and thus at the logical value '1'. The adder 192 has six outputs S0 . . . S5, which are connected to the data input of a clocked buffer register 194.

The register 194 consists e.g. of two individual buffer register components which can buffer six bits. The Q outputs of the register 194 are connected to one input of six AND gates 196A . . . 196F respectively, whose other inputs are each connected to the clear input. This clear input is at logical '1' in the normal operating state. The outputs of the AND gates are respectively connected to the inputs A0 . . . A5 of the adder 192. Thus the values at the outputs of the adder 192 are fed back to the inputs. The intermediately buffered value in the register 194 is strobed in by a clock signal CLK on a clock input CK. The input CK of the register 194 is connected to a two input OR gate OR 198 to whose one input the clock signal CLK is applied and whose other input is connected to the output of an AND gate AND 202 which has three inputs. One of these inputs is connected to the CLEAR input of the circuit arrangement 190 the second to the ENABLE input EN and the third to the output AK-A of the address comparator 204.

The bits 2, 6, 15, 8, 4 and 13 at the output of the pseudo-random generator PRBS 150 and the Q outputs of the register 194 are applied to a first logic circuit 206 in which these signals can be combined in various ways. The first logic circuit 206 has six outputs, two of which are applied directly to a second logic circuit 208 and the remaining four via a four bit adder 210. Output bits 10, 19, 5 and 14 of the pseudo-random generator 150 are also applied to the four bit adder 210. The remaining output bits 1, 16, 11, 18 and 9 of the pseudo-random generator 150 are applied to the second logic circuit 208.

Figure 14B:
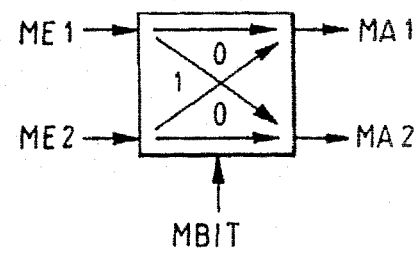
FIG. 14b) shows a circuit diagram of an M-box of the generator of FIG. 14a)

The first and second logic circuits 206 and 208 include E-BOX circuits, M-BOX circuits and/or adders. An M-BOX circuit is shown in FIG. 14b) and is essentially a reversing switch having the following truth table:

| Inputs | | | Outputs | |
|---|---|---|---|---|
| ME1 | ME2 | MBIT | MA1 | MA2 |
| 0 | 0 | 0 | 0 | 0 |
| 0 | 0 | 1 | 0 | 0 |
| 0 | 1 | 0 | 0 | 1 |
| 0 | 1 | 1 | 1 | 0 |
| 1 | 0 | 0 | 1 | 0 |
| 1 | 0 | 1 | 0 | 1 |
| 1 | 1 | 0 | 1 | 1 |
| 1 | 1 | 1 | 1 | 1 |

Figure 14C:
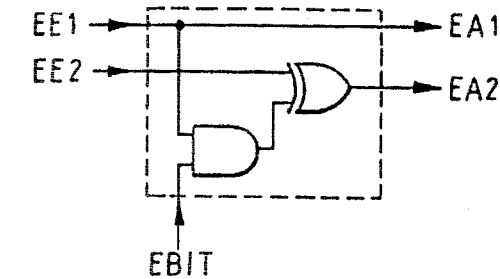
FIG. 14c) shows a circuit diagram of an E-box of the generator of FIG. 14a)

A detailed circuit diagram of an E-BOX circuit is shown in FIG. 14c). The E-BOX comprises an AND gate with two inputs and an Exclusive-OR gate, likewise with two inputs. The truth table for the E-BOX is as follows:

| Inputs | | | Outputs | |
|---|---|---|---|---|
| EE1 | EE2 | EBIT | EA1 | EA2 |
| 0 | 0 | 0 | 0 | 0 |
| 0 | 0 | 1 | 0 | 0 |
| 0 | 1 | 0 | 0 | 1 |
| 0 | 1 | 1 | 0 | 1 |
| 1 | 0 | 0 | 1 | 0 |
| 1 | 0 | 1 | 1 | 1 |
| 1 | 1 | 0 | 1 | 1 |
| 1 | 1 | 1 | 1 | 0 |

The six PERMUTATION ADDRESS outputs of the second logic circuit form the six outputs of the permutation generator. At these outputs of the circuit arrangment 2 there can thus be generated $2^6$=64 different permutation addresses PA0 . . . PA63.

A television field consists of e.g. a=6 blocks, each with 47 lines Z0 . . . Z46, i.e. 282 video lines as described previously. The sequence of the lines within each such block is permutated by the permutation generator.

The address comparator 204, whose six inputs are connected to the PERMUTATION ADDRESS outputs of the circuit arrangement 190 now checks the allowability of a permutation address. In the present example the addresses PA47 . . . PA63 represents impermissible addresses, since a block only has 47 lines. If a generated permutation address is impermissible, the address comparator generates a control signal, which is applied to the AND gate AND 202 and causes the generation of a new address. Impermissible permutation addresses are thus automatically filtered out and not used for the switching of the sequence of television lines.

A very large number of different permutations can be generated with the described permutation generator according to FIG. 14. It can be shown that the permutation generator can generate 720896 different permutations according to the issuance of 1048576 control words from the PRBS 150. This means that 720896/log2=19.46 bits of the 20 bits of the pseudo-random generator PRBS are used effectively. The efficiency of the permutation generator thus amounts to $2^{19.46}/2^{20}*100\%=68.8\%$.

Figure 15:
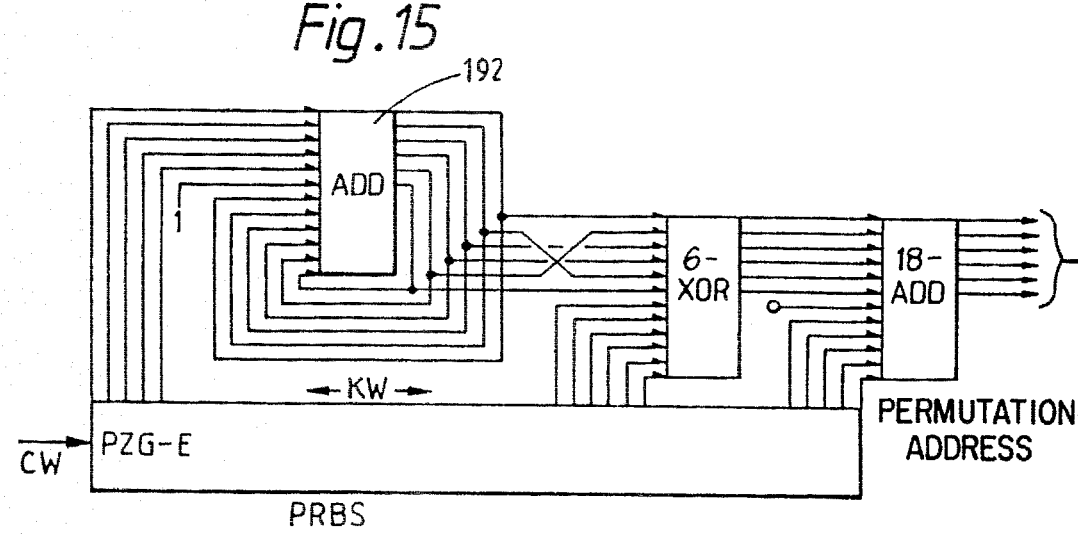
FIG. 15 shows an alternative embodiment of the permutation generator.

FIG. 15 shows a further, simplified embodiment of a permutation generator with a pseudo-random generator PRBS with n=16 outputs, a six bit adder 192 as in FIG. 14a) with its outputs fed back to its inputs, an XOR component 6 with six XOR gates and a further six bit adder 18 with six PERMUTATION ADDRESS outputs. Such a permutation generator, which has less than sixty implemented gate elements, is cost-effective, of small structure and nevertheless provides a very large number of different permutations.

The pseudo-random generator PRBS 150 in FIGS. 14a) and FIG. 15 is constructed as a feedback shift register or as a circuit which generates pseudo-random numbers in accordance with the Johnson theory. The generation of pseudo-random numbers with such a generator is also used as a solution to the so-called "unranking" problem in the generation of a plurality of permutations.

Various modifications to the embodiments described are possible and will occur to those skilled in the art. For example the block size may vary.

The system has been described in terms of the PAL standard and is suitable for all the major PAL standards, i.e. system I,B,G,D and H. For system M PAL, used in Brazil, the number of active picture lines per field is only 243 and the number of shuffled lines per field may be 240. This may be arranged as six blocks of 40 lines, 4 blocks of 60 lines or 5 blocks of 48 lines. The number of pixels per line is only 909 and the subcarrier frequency Fsc=3.57561149 MHz.

For system N PAL, used in some South American countries, the system is very similar to the system I PAL embodiment described, except that the lower sub-carrier frequency, 3.58205625 MHz requires a lower sample rate of 917.0064 samples per line.

For the NTSC standard such as is used in the United States of America and Japan, the number of lines per field and the block arrangement is the same as for system M PAL outlined above. In both cases the smallest block size is most desirable to minimise noise caused by field distortion and hum. The subcarrier frequency is higher, 3.579545 MHz and thus the sampling frequency and number of samples per line higher, 14.31818 MHz and 910 respectively. In both the system M and NTSC solutions outlined, 3 data lines are included in the active picture lines, the three unshuffled lines. These lines carry Videocrypt data. One line of the vertical blanking interval is also required for data. Alternatively, a data compression algorithm could be used to compress the data onto three lines.

The SECAM standard, used for example in France, is a 625 line system and uses the same block structure as the PAL example described. However, the phase locked loop requires modification. This may be achieved in two manners. Firstly, the PLL may be line locked, and secondly, one of the two colour difference sub-carriers only may be used and the system arranged as for the PAL example.

In this case, the sub-carrier used could be the (R-Y) carrier, the higher frequency of the two, which has a frequency of 4.406250 MHz giving 1128 pixels per line. Alternatively, the 4.250000 MHz sub-carrier could be used giving a sampling frequency of 17 MHz.

The system may be adapted for use with other standards such as the MAC family and extended to high definitions standards. It may be convenient to increase the number of blocks to 12×47 lines for future HDTV broadcasts or to increase the block size to 94 lines. Such modifications all fall within the scope of the invention which is defined in the following claims.

We claim:

1. A video signal encoder for providing a scrambled video signal output, comprising means for sampling an input video signal, means for digitising the sampled signal, means for subdividing the digitised sampled signal into a plurality of blocks of active picture lines, and means for shuffling the line order within each block according to a predetermined sequence to scramble the signal, characterised in that the colour bursts of shuffled lines remain in position and that the sampling frequency is an integral multiple of four times the frequency of the reference colour subcarrier of the video signal.

2. An encoder according to claim 1, wherein the sampling frequency $n4F_{sc}$ is locked to the phase and frequency of the colour burst of the video signal.

3. An encoder according to claim 2, wherein the sampling points are at 45° points on the reference subcarrier.

4. An encoder according to claims 1, 2 or 3, wherein the number of samples per line at $4F_{sc}$ is non-integral, comprising compensation means for adding to selected lines extra samples comprising the sum of omitted sample fractions.

5. An encoder according to claim 4, wherein each video line comprises 1135.0064 samples, and each line is treated as comprising 1135 samples, the compensating means adding 2 samples to a selected video line every video field.

6. An encoder according to claim 1, wherein the means for shuffling line order shuffles only active line period of active lines.

7. An encoder according to claim 1, wherein the subdividing means subdivides each field into an integral plurality of blocks of active picture lines.

8. An encoder according to claim 7, wherein each field is divided into five blocks, four blocks of which each comprise 56 active picture lines and the fifth block 59 active picture lines.

9. A video signal encoder according to claim 1, comprising means for synchronising the video signal and including means for generating a synchronisation window, means for monitoring the time difference between a given video line in adjacent video fields, and means for resynchronising the encoder if the monitored time difference does not fall within the period of the synchronisation window.

10. An encoder according to claim 2, comprising a digital phase lock loop having analog-to-digital convertor for converting an analog input signal to a digital signal, a burst-phase detector for detecting the phase of the colour bursts of the lines of digitised video input signal which include a colour burst, and means for forming a n error signal in accordance with variations in the detected phase of the colour burst to produce a voltage control signal for the voltage controlled crystal oscillator of the clock generator.

11. An encoder according to claim 10, wherein the means for producing an error signal in the digital phase lock loop comprises a pulse width modulator and a loop filter.

12. A video signal decoder for providing a clear output suitable for display from a received scrambled video signal, comprising receiving means for receiving the scrambled signal, sampling means for sampling the received signal, digitising means for digitising the sampled signal, subdividing means for subdividing the digitised sampled signal into a plurality of blocks of active picture lines, and shuffling means for shuffling the order of lines in each block according to the inverse of the predetermined shuffling sequence used to scramble the signal, characterised in that the received colour bursts of shuffled lines remain in position and in that the sampling frequency is an integral multiple of four times the frequency of the reference colour subcarrier of the video signal.

13. A decoder according to claim 12, wherein the sampling frequency $n4F_{sc}$ is locked to the phase and frequency of the colour burst of the video signal.

14. A decoder according to claim 13, wherein the sampling points are at 45° points on the reference subcarrier.

15. A decoder according to claims 12, 13 or 14, wherein the means for shuffling line order within blocks shuffles only active line periods of active picture lines.

16. A decoder according to claim 12, wherein the subdividing means subdivides each field into an integral plurality of blocks of active picture lines.

17. A decoder according to claim 16, wherein each field comprises five blocks, four blocks each comprising 56 active picture lines and one block comprising 59 active picture lines.

18. A decoder according to claim 12, comprising means for synchronising the received video signal and including means for generating a synchronisation window, means for monitoring the time difference between a given video line in adjacent video fields, and means for resynchronising the decoder if the monitored time difference does not fall within the period of the synchronisation window.

19. A decoder according to claim 12, comprising means for generating and re-inserting into each line of the signal a clean black clamp level and means for passing unmodified the colour burst for each line.

20. A decoder according to claim 19, wherein the means for reinserting the black level comprises a bandpass filter for passing a selected portion of an input video signal, means for adding the black clamp level to the output of the bandpass filter to provide a black clamp level and means responsive to a control signal for inserting the black clamp level into the video signal.

21. A decoder according to claim 20, wherein the input video signal is a digital signal and the inserting means comprises a multiplexer under the control of a video synchronising signal.

22. A decoder according to claim 13, comprising a digital phase lock loop having analog-to-digital convertor for converting an analog input signal to a digital signal, a burst-phase detector for detecting the phase of the colour bursts of the lines of digitised video input signal which include a colour burst, and means for forming a n error signal in accordance with variations in the detected phase of the colour burst to produce a voltage control signal for the voltage controlled crystal oscillator of the clock generator.

23. A decoder dependent on claim 22, wherein the means for producing an error signal in the digital phase lock loop comprises a pulse width modulator and a loop filter.

24. A video signal transmission system comprising:

at a transmitter:

an analog video signal source;

an encoder for scrambling the analog source comprising means for sampling the source signal at a frequency an integral multiple of four times the frequency of the reference colour sub-carrier of the video signal, means for digitising the sampled signal, means for sub-dividing active picture lines of the signal into a number of blocks of lines, and means for shuffling the order of lines within each block according to a predetermined sequence to produce a scrambled signal, wherein the colour bursts of shuffled lines remain in position; and means for transmitting the scrambled video signal in analog form; and at a receiver;

means for receiving the scrambled video signal;

a decoder for providing a clear video signal for display or storage from the scrambled received signal, comprising means for sampling the received signal at a frequency an integral multiple of four times the frequency of the reference colour sub-carrier of the video signal, means for digitising the sampled signal, means for sub-dividing the digitised sampled signal into a number of blocks of lines and for shuffling the order of lines within each block according to a predetermined shuffling sequence the inverse of that applied to shuffle the lines at the transmitter to produce a clear signal, wherein the colour bursts of shuffled lines remain in position; and means for displaying or storing the clear signal.

* * * * *